United States Patent [19]

Komori et al.

[11] Patent Number: 5,162,233
[45] Date of Patent: Nov. 10, 1992

[54] METHOD OF DETECTING AND ANALYZING IMPURITIES

[75] Inventors: Junko Komori; Yoji Mashiko, both of Itami, Japan

[73] Assignee: Mitsubishi Denki Kabushiki Kaisha, Japan

[21] Appl. No.: 153,921

[22] Filed: Feb. 9, 1988

[30] Foreign Application Priority Data

Dec. 16, 1987 [JP] Japan .................. 62-316121

[51] Int. Cl.$^5$ .......................... G01N 1/00; B08B 5/04
[52] U.S. Cl. ............................. 436/155; 436/175; 73/863.11; 356/36; 134/21; 134/26
[58] Field of Search .............. 436/155, 175, 807, 807, 436/164; 73/863, 863.11; 356/36; 134/25.4, 21, 26

[56] References Cited

U.S. PATENT DOCUMENTS

| | | | |
|---|---|---|---|
| 3,878,392 | 4/1975 | Yew et al. | 250/307 X |
| 3,904,364 | 9/1975 | Dodson | 356/36 X |
| 4,271,022 | 6/1981 | Dixon et al. | 356/36 X |
| 4,351,801 | 9/1982 | Bartke | 436/155 X |
| 4,452,642 | 6/1984 | Dietz et al. | 134/21 X |
| 4,740,249 | 4/1988 | McConnell | 134/25.4 |
| 4,760,254 | 7/1988 | Pierce et al. | 250/307 X |

OTHER PUBLICATIONS

*Chemical Principles,* Dickerson, R. E., Gray H. B., Haight, G. P., 3rd Ed, The Benjamin/Cummings Pub. Co., Inc., Calif., 1979.
"The PHI 5000 Series ESCA Systems", Perkin-Elmer Co., Ltd., PHI Data Sheet 1066 Sep. 1983 10M.

*Primary Examiner*—Robert J. Warden
*Assistant Examiner*—Amalia Santiago
*Attorney, Agent, or Firm*—Leydig, Voit & Mayer

[57] ABSTRACT

A method of detecting and analyzing impurities wherein a substrate is cleaned by heating it under vacuum, a liquid sample is dropped on a surface of the substrate under vacuum which vacuum is less than that of the previous step, the liquid sample which has thus been dropped on the substrate is dried by reducing the pressure of the atmosphere surrounding the substrate, and impurities contained in the liquid sample are detected and analyzed by examining the surface of the substrate. Thus, this method is adapted to minimize the risk of any foreign matter becoming mixed with the sample liquid, to thus ensure a high level of precision in the detection and analysis of impurities.

8 Claims, 3 Drawing Sheets

METHOD OF DETECTING AND ANALYZING IMPURITIES

BACKGROUND OF THE INVENTION

1. Field of the Invention

The present invention relates to a method of detecting and analyzing impurities contained in a liquid sample with a high level of precision.

2. Description of the Related Art

A known method of detecting and analyzing impurities in a liquid sample will be described with reference to FIG. 9. A liquid sample 1 is contained in a pipette 2. A substrate 3 is disposed below the pipette 2 so that the liquid sample 1 can be dropped on the substrate 3 and be transferred thereby to an analyzing device, etc.

The substrate 3 has previously been subjected to the following treatment. Namely, it is cleaned by soaking it in a cleaning liquid which is, for instance, a hydrofluoric-acid based acid or a mixture of sulfuric acid and nitric acid, thereby removing any foreign matter attached to the surfaces of the substrate 3. After the cleaning, the substrate 3 is dried by, for instance, applying thereto a jet of nitrogen gas.

A suitable amount of the liquid sample 1 is discharged from the pipette 2 and is dropped on the surface of the substrate 3 which has been cleaned and dried in the above fashion. Thereafter, the liquid sample 1 on the substrate 3 is allowed to dry or is dried by heating the substrate 3 in a heating device (not shown). By this drying, impurities contained in the liquid sample 1 become attached to the surface of the substrate 3.

Subsequently, the substrate 3 is placed in an ordinary solid analyzing device (not shown) in which impurities attached to the surface of the substrate 3 are analyzed.

The known method is adapted to detect and analyze impurities contained in the liquid sample 1 in the above-mentioned manner. This known method of detecting and analyzing impurities, however, involves the following disadvantages.

First, with the known method, there is a risk that foreign matter which may possibly be contained in the cleaning liquid used to clean the substrate 3 may become attached to the substrate 3 while it is cleaned. Foreign matter which is not in the cleaning liquid may also become attached to the substrate 3 during the cleaning.

Second, since the substrate 3 is simply soaked in the cleaning liquid according to the known method, there is a risk that foreign matter on the surfaces of the substrate 3 may not be removed to a sufficient extent and may remain attached to the surface.

Thirdly, with the known method, there is a risk that, during the drying of the liquid sample 1 which has been dropped on the substrate 3, foreign matter may become mixed with the liquid sample 1.

Lastly, if the substrate 3 is heated according to the known method so that the liquid sample 1 dropped on the substrate 3 can dry quickly, there is a risk that certain types of liquid samples 1 may decompose at the temperatures used to heat the substrate 3. Thus, the heating process has to be conducted carefully in this respect.

Because of these disadvantages, it has been difficult to achieve high levels of precision in the detection and analysis of impurities contained in a liquid sample by using the known method.

SUMMARY OF THE INVENTION

The present invention has the objective of overcoming the disadvantages of the prior art. It is a primary object of the present invention to provide a method of detecting and analyzing impurities contained in a liquid sample, which is capable of minimizing the risk of any foreign matter contaminating the liquid sample and is thus capable of detecting and analyzing the impurities with a high level of precision.

To this end, a method of detecting and analyzing impurities in a liquid sample in accordance with the present invention comprises:

a first step of cleaning a substrate by heating it under vacuum;

a second step of dropping a liquid sample under vacuum which vacuum is less than that of the first step on a surface of the substrate which has been cleaned in the first step;

a third step of drying the liquid sample which has been dropped on the substrate in the second step by reducing the pressure of the atmosphere surrounding the substrate; and a fourth step of detecting and analyzing impurities contained in the liquid sample by examining the surface of the substrate which has been dried in the third step.

According to the method of the present invention, the first step is such that the substrate is heated under a high degree of vacuum so that any foreign matter attached to the surface of the substrate is subjected to thermal energy and is thus removed from the surface with ease, whereby the substrate can be completely cleaned.

Further, according to the method of the present invention, the third step is such that the sample liquid is dried by reducing the pressure of the atmosphere surrounding the substrate, thus making it possible to reduce the period required for drying and thus minimize the risk of any foreign matter becoming mixed with the liquid sample.

DESCRIPTION OF THE PREFERRED EMBODIMENTS

An embodiment of the present invention will be described hereunder with reference to the accompanying drawings.

Figure 1:
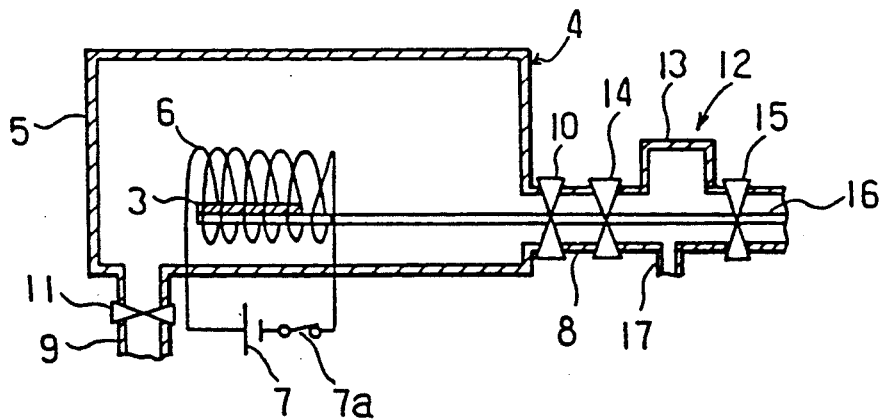
FIGS. 1 through 8 are sectional views of various devices used in an embodiment of a method of detecting and analyzing impurities in accordance with the present invention, these figures being arranged in the order of the steps of the method.

FIGS. 1 through 8 schematically illustrate various devices in section which are used in an embodiment of a method of detecting and analyzing impurities in accordance with the present invention. These drawings are arranged in an order which facilitates explanation of the method step by step, and the same reference numerals are used in these drawings to denote the same or corresponding components or elements. Referring to FIG. 1, a cleaning device 4 has a chamber 5. A heater 6 for heating a substrate 3 is disposed within the chamber 5. A power source 7 and a switch 7a through which the power source 7 can be connected to the heater 6 for supplying electric power thereto are disposed outside the chamber 5. A port 8 through which the substrate 3 can be placed into and taken out of the chamber 5, and a port 9 used for purging are disposed on the corresponding side portions of the chamber 5. These ports 8 and 9 are provided with valves 10 and 11, respectively, so that they can be opened and closed by the corresponding valves. When both valves 10 and 11 are closed, a sealed space is formed within the chamber 5. The port 9 is connected to a pressure reduction device (not shown) such as a vacuum pump.

The cleaning device 4 constructed as described above can be connected at the port 8 with a transfer vessel device 12. The transfer vessel device 12 is provided for enabling the substrate 3 to be transferred while maintaining it under a vacuum, and comprises a vessel body 13, two valves 14 and 15 mounted on the vessel body 13, and a rod 16 for moving the substrate 3. The vessel body 13 has a port 17 which is connected to a pressure reduction device (not shown) such as a vacuum pump, to allow purging.

An operation of detecting and analyzing impurities contained in a liquid sample is performed in the following manner. First, the transfer vessel device 12 which receives therein a substrate 3 is connected to the port 8 of the cleaning device 4, as shown in FIG. 1. The substrate 3 is, for instance, a silicon wafer. Thereafter, the valves 10 and 14 are opened, and the substrate 3 is placed inside the heater 6 in the chamber 5 of the cleaning device 4 through the port 8 by using the rod 16. With this condition in which the valves 10 and 14 are open, the valve 11 at the port 9 is opened, and, with the valve 15 being kept closed, the pressures within the chamber 5 of the cleaning device 4 and the vessel body 13 of the transfer vessel device 12 are reduced by means of the corresponding pressure reduction devices. When a degree of vacuum of about $1 \times 10^{-10}$ torr has been obtained within each of the chamber 5 and the vessel body 13, the valves 10 and 14 are closed. The switch 7a is then closed to connect the power source 7 to the heater 6, and the substrate 3 is heated to a temperature of at least 1000° C.

During this heating, foreign matter such as heavy metals attached to the substrate 3 is subjected to thermal energy and is allowed to diffuse from the surfaces of the substrate 3 into the vacuum, whereby the substrate 3 is completely cleaned.

Figure 2:
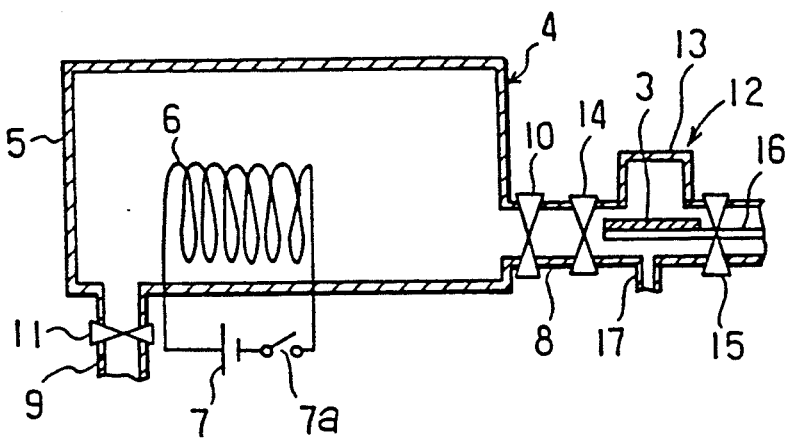

Thereafter, the switch 7a is opened to stop the supply of electricity to the heater 6. The valves 10 and 14 are opened, and the substrate 3 is moved from the chamber 5 of the cleaning device 4 to the vessel body 13 of the transfer vessel device 12 by using the rod 16, as shown in FIG. 2. At this point, a high degree of vacuum of about $1 \times 10^{-10}$ torr already prevails within the vessel body 13.

Figure 3:
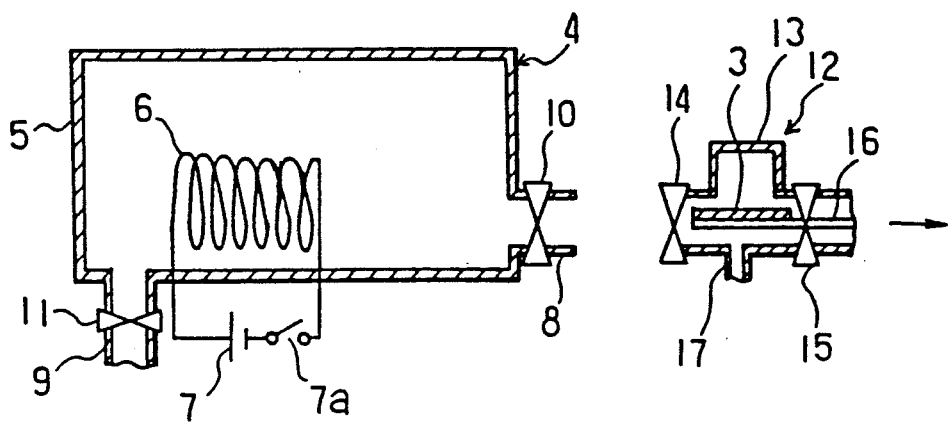
Figure 4:
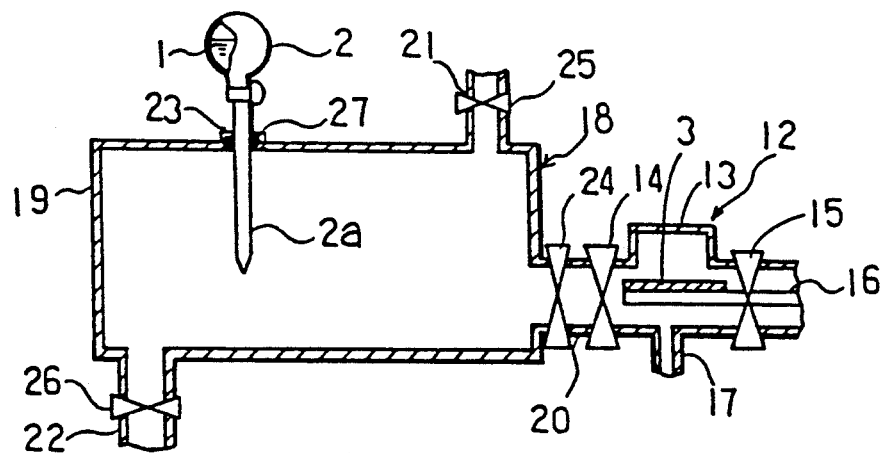

The valves 10 and 14 are closed, and the transfer vessel device 12 is disconnected from the port 8 of the cleaning device 4, as shown in FIG. 3. The transfer vessel device 12 is then connected to a sample dropping device 18, as shown in FIG. 4.

The sample dropping device 18 has a chamber 19 which is provided with four ports 20 to 23. A first port 20 is provided to allow the substrate 3 to be placed into and taken out of the chamber 19 and has a valve 24. A second port 21 is connected to an inert gas supply device (not shown) for enabling introduction of inert gas into the chamber 19 and has a valve 25. A third port 22 is connected to a pressure reduction device such as a vacuum pump to allow purging and has a valve 26. A fourth port 23 is provided for enabling insertion of the tip portion 2a of a pipette 2 from the outside of the chamber 19 to the inside. The fourth port 23 has an O-ring 27 so that the pipette 2 can be inserted through the port 23 in an airtight manner. The pipette 2 receives a liquid sample 1 which is to be analyzed.

The transfer vessel device 12 is connected to the first port 20 of the sample dropping device 18 constructed as described above, as shown in FIG. 4.

Figure 5:
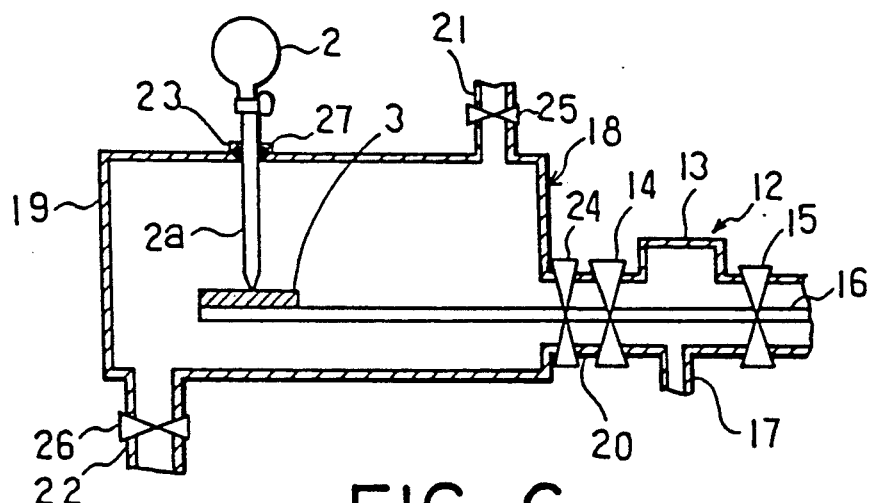

The valves 24 and 26 are opened, and, with the valve 25 being kept closed, the pressure within the chamber 19 of the sample dropping device 18 is reduced to a vacuum of about $1 \times 10^{-10}$ torr by means of the pressure reducing device. During this operation, the valve 14 of the transfer vessel device 12 remains closed When the pressure reducing operation is completed, the valve 14 is opened. The substrate 3 is then placed into the chamber 19 of the sample dropping device 18 by using the rod 16 and is located immediately below the pipette 2, as shown in FIG. 5.

Thereafter, the valves 14, 24, and 26 are closed while the valve 25 in the second port 21 is opened, and a clean inert gas, such as nitrogen or argon, is introduced into the chamber 19 through the port 21 by means of the inert gas supply device, so as to obtain an atmospheric pressure within the chamber 19. When the desired pressure has been obtained, the tip of the pipette 2 is brought as close as possible to the surface of the substrate 3, and the liquid sample 1 is discharged from the pipette 2 and dropped on the surface of the substrate 3 in a small amount. The thus dropped liquid sample 1 forms a hemispheric shape on the surface of the substrate 3 because of surface tension.

Subsequently, the valve 25 is closed whereas the valves 24 and 26 are opened, and the pressure within the chamber 19 is reduced by means of the pressure reduction device through the port 22. By this reduction in the pressure within the chamber 19, the liquid sample 1 on the substrate 3 quickly dries, after which impurities contained in the liquid sample 1 remain on the surface of the substrate 3.

Figure 6:
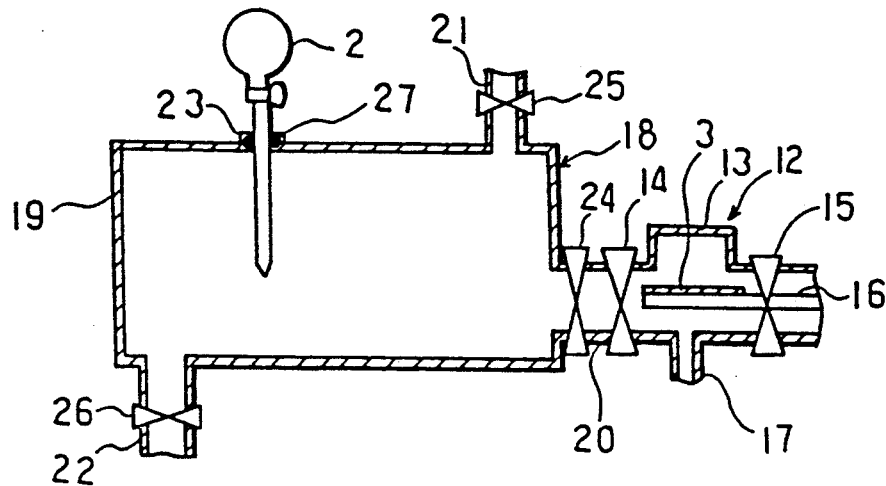
Figure 7:
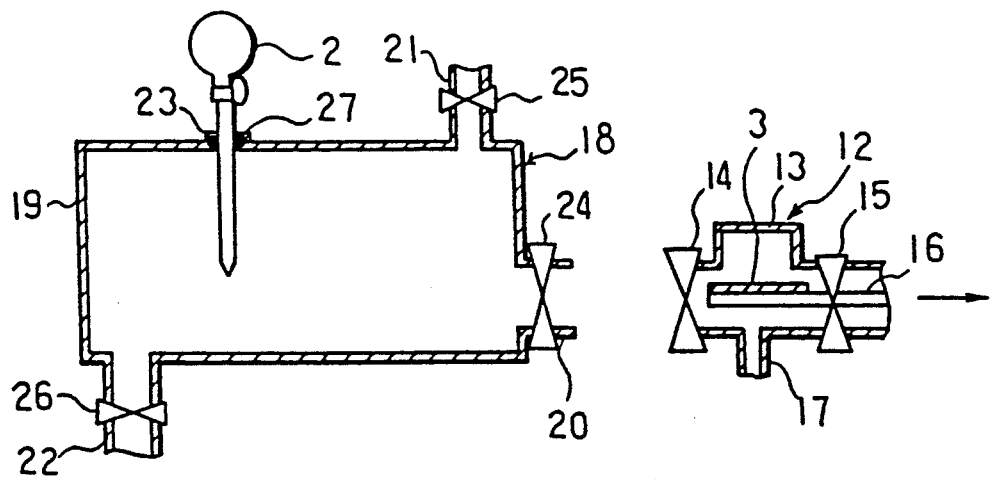

When a vacuum of about $1 \times 10^{-10}$ torr has been obtained within the chamber 19, the valve 14 of the transfer vessel device 12 is opened. The substrate 3 is then moved from the sample dropping device 18 to the vessel body 13 of the transfer vessel device 12 by using the rod 16, as shown in FIG. 6. At this point, the internal pressure within the vessel body 13 remains at a high degree of vacuum of about $1 \times 10^{-10}$ torr Subsequently, the valves 14 and 24 are closed, and the transfer vessel device 12 is disconnected from the port 20 of the sample dropping device 18, as shown in FIG. 7. The transfer vessel device 12 is then connected to a solid analyzing device 28, as shown in FIG. 8.

Figure 8:
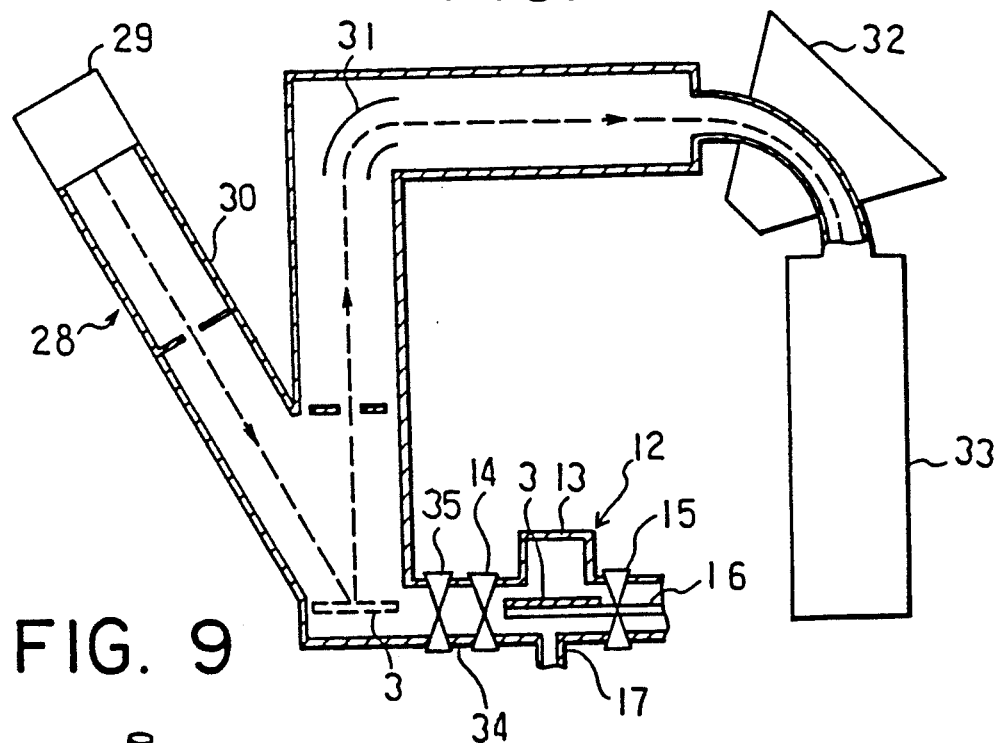
Figure 9:
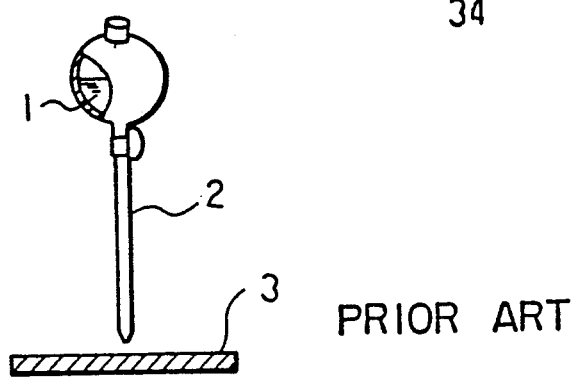
FIG. 9 is a view used to explain a known method of detecting and analyzing impurities.

The solid analyzing device 28 shown in FIG. 8 is, for instance, an ordinary secondary ion mass spectroscope (SIMS) which comprises an ion gun 29, an ion passage 30, an energy selector 31, a magnetic field selector 32, and a detector 33. The interior of the device 28 is maintained at a high degree of vacuum by means of a pressure reduction device (not shown). A port 34 for allowing the substrate 3 to be placed into and taken out of the ion passage 30 is provided on a side portion of the passage 30. A valve 35 is mounted on the port 34.

The transfer vessel device 12 is connected to the port 34 of the solid analyzing device 28 constructed as described above.

The valves 14 and 35 are opened, and the substrate 3 is placed into the passage 30 by using the rod 16. The valve 35 is then closed.

Thereafter, an ion beam is radiated from the ion gun 29 onto the surface of the substrate 3, whereby impurities remaining on the surface of the substrate 3 are ionized and are discharged as secondary ions. The secondary ions pass through the energy selector 31 and the magnetic field selector 32, whereby they are subjected to mass analysis. Thereafter, quantitative measurement is conducted by means of the detector 33.

In this way, the detection and analysis of impurities contained in a liquid sample can be conducted while minimizing the risk of any foreign matter contaminating the liquid sample.

Although in the foregoing description the dropping of the liquid sample 1 is conducted within the sample dropping device 18 in an inert gas atmosphere under an atmospheric pressure, this process may alternatively be conducted after clean inert gas or air has been introduced into the chamber 19 through the port 21 to obtain a degree of vacuum of about $1 \times 10^{-3}$ torr within the chamber 19, which vacuum is less that of the cleaning step. If the dropping process is conducted in the latter manner, the subsequent process of reducing the pressure within the chamber 19 to obtain a higher degree of vacuum can be performed within a shorter period of time.

The pipette 2 containing the liquid sample 1 is disposed at the port 23 of the sample dropping device 18 through the O-ring 27 in such a manner as to be detachable therefrom. Therefore, if a plurality of pipettes 2 which each contain a different liquid sample 1 are prepared, the replacement of a liquid sample with another can be done simply by replacing the corresponding pipettes.

Although in the foregoing embodiment, the substrate 3 is made of silicon, the invention is not limited thereto. The substrate 3 may be made of any other material so long as it can withstand the heating conducted within the cleaning device 4.

Devices which may be used as the solid analyzing device 28 include, in addition to a SIMS, ordinary analyzing devices such as an auger electron spectroscope and an X-ray micro analyzer.

Although in the foregoing embodiment, a pressure of about $1 \times 10^{-10}$ torr is obtained within the cleaning device 4 during the cleaning of the substrate 3, within the sample dropping device 18 after the dropping of the liquid sample 1, and within the transfer vessel device 12, this is not to be construed as limiting the invention. Instead, a pressure of about $1 \times 10^{-3}$ to $1 \times 10^{-7}$ torr may be used, and this could provide an effect which is similar to the above to a satisfactory extent.

As described above, with the method of detecting and analyzing impurities in accordance with the present invention, a substrate is cleaned by being heated under a high degree of vacuum, and a liquid sample which has been dropped on the substrate is dried quickly by reducing the pressure of the atmosphere surrounding the substrate. Therefore, it is possible to minimize the risk of any foreign matter becoming mixed with the sample, and thus conduct detection and analysis of impurities contained in the liquid sample with a high level of precision.

What is claimed is:

1. A method of detecting and analyzing impurities comprising:

a first step of cleaning a substrate by heating it under vacuum;

a second step of dropping a liquid sample under vacuum, which vacuum is less than that of the first step on a surface of said substrate which has been cleaned in said first step;

a third step of drying said liquid sample which has been dropped on said substrate in said second step by reducing the pressure of the atmosphere surrounding said substrate; and a fourth step of detecting and analyzing impurities contained in said liquid sample by examining said surface of said substrate which has been dried in said third step.

2. A method of detecting and analyzing impurities according to claim 1, wherein said first step is conducted in a first sealed space, said second and third steps are conducted in a second sealed space, and said fourth step is conducted in a third sealed space, said substrate being transferred from said first sealed space to said second sealed space and from said second sealed space to said third sealed space while said substrate is maintained under a high degree of vacuum.

3. A method of detecting and analyzing impurities according to claim 1, wherein said substrate comprises a silicon wafer.

4. A method of detecting and analyzing impurities according to claim 3, wherein said substrate is heated to a temperature of at least 1000° C. in said first step.

5. A method of detecting and analyzing impurities according to claim 1, wherein said first step is conducted under a high degree of vacuum of about $1 \times 10^{-10}$ torr.

6. A method of detecting and analyzing impurities according to claim 1, wherein said second step is conducted in an atmosphere having a degree of vacuum of about $1 \times 10^{-3}$ torr.

7. A method of detecting and analyzing impurities according to claim 1, wherein said second step is conducted in an inert gas atmosphere.

8. A method of detecting and analyzing impurities according to claim 1, wherein the pressure of said atmosphere surrounding said substrate is reduced to a high degree of vacuum of about $1 \times 10^{-10}$ torr.

* * * * *